(12) United States Patent
Moustafa et al.

(10) Patent No.: US 12,136,489 B2
(45) Date of Patent: Nov. 5, 2024

(54) PREDICTIVE RECOMMENDATION SYSTEMS USING COMPLIANCE PROFILE DATA OBJECTS

(71) Applicant: Optum Services (Ireland) Limited, Dublin (IE)

(72) Inventors: Karim Mahmoud Mohamed Moustafa, Dublin (IE); Harutyun Shahumyan, Dublin (IE); Gevorg Poghosyan, Dublin (IE); Kieran M. Cooney, Dublin (IE); Lisa E. Walsh, Dublin (IE)

(73) Assignee: Optum Services (Ireland) Limited, Dublin (IE)

( * ) Notice: Subject to any disclaimer, the term of this patent is extended or adjusted under 35 U.S.C. 154(b) by 358 days.

(21) Appl. No.: 17/528,041

(22) Filed: Nov. 16, 2021

(65) Prior Publication Data

US 2023/0154596 A1  May 18, 2023

(51) Int. Cl.
*G06Q 30/02* (2023.01)
*G16H 20/00* (2018.01)
(Continued)

(52) U.S. Cl.
CPC ............ *G16H 40/20* (2018.01); *G16H 20/00* (2018.01); *G16H 50/70* (2018.01)

(58) Field of Classification Search
CPC ........ G16H 40/20; G16H 20/00; G16H 50/70; G16H 20/40; G16H 20/60; G16H 20/10; G16H 50/20; G16H 70/20
See application file for complete search history.

(56) References Cited

U.S. PATENT DOCUMENTS

| 8,103,524 B1 | 1/2012 | Rogers et al. |
| 8,412,542 B2 * | 4/2013 | Mok ...................... G16H 40/20 |
| | | 705/2 |

(Continued)

FOREIGN PATENT DOCUMENTS

| CA | 3181594 A1 * | 11/2021 | ............... G06E 1/00 |
| KR | 10-2020-0061097 A | 6/2020 | |
| WO | WO 2015/023674 A1 * | 2/2015 | ............ G06F 3/048 |

OTHER PUBLICATIONS

Volker Tresp; J. Marc Overhage; Markus Bundschus; Shahrooz Rabizadeh; Peter A, Fasching; Shipeng Yu, Going Digital: A Survey on Digitalization and Large-Scale Data Analytics in Healthcare (English), Proceedings of the IEEE (vol. 104, Issue: 11, pp. 2180-2206), Nov. 2, 2016 (Year: 2016).*

(Continued)

*Primary Examiner* — Marilyn G Macasiano
(74) *Attorney, Agent, or Firm* — Alston & Bird LLP

(57) ABSTRACT

Various embodiments provide methods, apparatus, systems, computing entities, and/or the like, for performing predictive recommendation. In one example embodiment, a method is provided. The method includes generating guideline data objects for a plurality of service need conditions. The method includes generating a compliance profile data object for each of a plurality of provider entities. The compliance profile data object for a provider entity includes compliance scores with respect to the plurality of service need conditions, a compliance score determined using procedural record data objects associated with each provider entity and the guideline data objects. The method further includes selecting a subset of the plurality of provider entities according to the compliance profile data object for each provider (Continued)

entity. The method further includes performing at least one automated recommendation-based action based at least in part on the selected subset.

19 Claims, 8 Drawing Sheets

(51) Int. Cl.
*G16H 40/20* (2018.01)
*G16H 50/70* (2018.01)

(56) References Cited

U.S. PATENT DOCUMENTS

| | | | |
|---|---|---|---|
| 8,489,418 B2 | 7/2013 | Gustafson et al. | |
| 10,854,334 B1* | 12/2020 | McNair | G16H 50/20 |
| 10,861,597 B2 | 12/2020 | Norris et al. | |
| 10,978,179 B2* | 4/2021 | Beltre | G06Q 50/22 |
| 11,011,266 B2 | 5/2021 | Burger et al. | |
| 2005/0234306 A1* | 10/2005 | Schulte | G16H 10/20 |
| | | | 128/920 |
| 2016/0147953 A1* | 5/2016 | Menon | G16H 10/20 |
| | | | 705/3 |
| 2017/0262604 A1* | 9/2017 | Francois | G16H 10/60 |
| 2019/0043606 A1 | 2/2019 | Roots et al. | |
| 2020/0005922 A1 | 1/2020 | Alhimiri | |
| 2021/0043310 A1 | 2/2021 | Valuck et al. | |
| 2021/0082549 A1 | 3/2021 | Hampden et al. | |
| 2021/0209119 A1 | 7/2021 | Claussenelias et al. | |

OTHER PUBLICATIONS

Zoran Milosevic, Enabling scalable AI for Digital Health: Interoperability, consent and ethics support(English), 2021 IEEE 25th International Enterprise Distributed Object Computing Workshop (EDOCW) (2021, pp. 18-27), Oct. 1, 2021 (Year: 2021).*

"Precision Navigation," Navigation—Health[at]Scale Technologies, (5 pages), (article, online), [Retrieved from the Internet Feb. 23, 2022] <URL: https://healthatscale.com/navigation/>.

Adomavicius, Gediminas et al. "Towards the Next Generation of Recommender Systems: A Survey of the State-of-the-Art and Possible Extensions," IEEE Transactions on Knowledge and Data Engineering, vol. 17, No. 6, pp. 734-749, Available online: http://pages.stern.nyu.edu/~atuzhili/pdf/TKDE-Paper-as-Printed.pdf.

Fang, Hui et al. "Probabilistic Models for Expert Finding," European Conference on Information Retrieval, Apr. 2, 2007, (12 pages), Springer, Berlin, Heidelberg.

Jiang, Hongxun et al. "How to Find Your Appropriate Doctor: An Integrated Recommendation Framework in Big Data Context, " 2014 IEEE Symposium on Computational Intelligence in Healthcare and e-health (CICARE), Orlando, FL, (Year: 2014), pp. 154-158, DOI: 10.1109/CICARE.2014.7007848.

Konstan, Joseph A. "Introduction to Recommender Systems: Algorithms and Evaluation," ACM Transactions on Information Systems, vol. 22, No. 1, Jan. 2004, pp. 1-4, DOI: 10.1145/963770.963771.

McDonald, David W. et al. "Expertise Recommender: A Flexible Recommendation System and Architecture," Proceedings of the 2000 ACM Conference on Computer Supported Cooperative Work, Dec. 2000, pp. 231-240, DOI: 10.1145/358916.358994.

Mustaqeem, Anam et al. "A Modular Cluster Based Collaborative Recommender System for Cardiac Patients," Artificial Intelligence in Medicine, vol. 102:101761, Jan. 2020, (ePub: Nov. 16, 2019), DOI: 10.1016/j.artmed.2019.101761.

Reboussin, David M. et al. "Systematic Review for the 2017 ACC/AHA/AAPA/ABC/ACPM/AGS/APhA/ASH/ASPC/NMA/PCNA Guideline for the Prevention, Detection, Evaluation, and Management of High Blood Pressure in Adults: A Report of the American College of Cardiology/American Heart Association Task Force on Clinical Practice Guidelines," Hypertension, vol. 71, No. 6, Jun. 2018, pp. e116-135, DOI: 10.1161/HYP.0000000000000067.

Resnick, Paul et al. "Recommender Systems—Introduction to the Special Section," Communications of the ACM, vol. 41, No. 3, Mar. 1997, pp. 56-58, DOI: 10.1145/245108.245121.

Sanaeifar, Ali et al. "SEPHYRES 1: A Physician Recommender System Based on Semantic Pain Descriptors and Multifaceted Reasoning," International Journal of Collaborative Research on Internal Medicine & Public Health, vol. 10, No. 1, (Year: 2018), pp. 735-746.

Shapiro, D.W. et al. "Containing Costs While Improving Quality of Care: The Role of Profiling and Practice Guidelines," Annual Review of Public Health, vol. 14, (Year: 1993), pp. 219-241, Available online: https://www.annualreviews.org/doi/pdf/10.1146/annurev.pu.14.050193.001251.

Villacorta, Reginald et al. "Determinants of Healthcare Provider Recommendations for Influenza Vaccinations," Preventive Medicine Reports, vol. 2, Apr. 28, 2015, pp. 355-370, DOI: 10.1016/j.pmedr.2015.04.017.

Wang, Chen et al. "The Research of Doctors Recommendation Algorithm based on Clustering and Collaborative Filtering," In Proceedings of the 23rd International Conference on Industrial Engineering and Engineering Management 2016, Mar. 8, 2017, pp. 233-237, Atlantis Press, Paris, DOI: 10.2991/978-94-6239-255-7_42.

Woolf, Steven H. et al. "Potential Benefits, Limitations, and Harms of Clinical Guidelines," The BMJ, vol. 318, No. 7182, Feb. 20, 1999, pp. 527-530, DOI: 10.1136/bmj.318.7182.527.

Yang, Yan et al. "Doctor Recommendation Based on an Intuitionistic Normal Cloud Model Considering Patient Preferences," Cognitive Computation, vol. 12, Dec. 6, 2018, pp. 460-478, DOI: https://doi.org/10.1007/s12559-018-9616-3.

* cited by examiner

PREDICTIVE RECOMMENDATION SYSTEMS USING COMPLIANCE PROFILE DATA OBJECTS

BACKGROUND

Various embodiments of the present disclosure address technical challenges related to performing predictive recommendation systems and provide solutions that improve the computational efficiency, operational reliability, and/or operational throughput of predictive recommendation systems.

BRIEF SUMMARY

In general, embodiments of the present disclosure provide methods, apparatus, systems, computing devices, computing entities, and/or the like for performing predictive recommendations. For example, certain embodiments of the present disclosure describe a compliance evaluation system and operations performed by said system, and the compliance evaluation system can be integrated, can comprise, can be coupled with, and/or the like various example recommendation systems in order to recommend one or more entities based at least in part on multiple factors including at least provider compliance with defined guidelines.

In particular, provider entities (e.g., healthcare providers, groups or cohorts of healthcare providers, hospitals, organizations) are evaluated for compliance with respect to each of a set of service need conditions based at least in part on procedures and treatments performed by the provider entities, in various embodiments. Provider compliance may be evaluated using guidelines extracted from reference datasets. For example, an extracted guideline may identify recommended actions, drugs, procedures, and/or the like or alternatively may identify non-recommended or harmful actions, drugs, procedures, and/or the like. In various embodiments, selection of provider entities for recommendation to a patient is based at least in part on provider compliance with respect to specific service need conditions relevant to the patient (e.g., at risk, diagnosed with).

In accordance with one aspect, a computer-implemented method is provided. The computer-implemented method may include generating a plurality of guideline data objects for a plurality of service need conditions. The method may further include generating, for each of a plurality of provider entities, a compliance profile data object including a plurality of compliance scores for the provider entity with respect to the plurality of service need conditions. Generating the compliance profile data object for a particular provider entity includes: for each given service need condition of the plurality of service need conditions: (i) retrieving one or more procedural record data objects each describing a treatment provided by the particular provider entity for the given service need condition, and (ii) determining a compliance score of the particular provider entity for the given service need condition using the one or more procedural record data objects and a subset of the plurality of guideline data objects that are associated with the given service need condition. Generating the compliance profile data object for the particular provider entity further includes determining the compliance profile data object based at least in part on each compliance score. The method may further include selecting a selected subset of the plurality of provider entities according to the compliance profile data object for each provider entity. The method may further include performing at least one automated recommendation-based action based at least in part on the selected subset.

In accordance with another aspect, a computer program product is provided. The computer program product may include at least one computer-readable storage medium having computer-readable program code portions stored therein, the computer-readable program code portions including executable portions configured to cause at least one processor to generate a plurality of guideline data objects for a plurality of service need conditions. The computer-readable program code portions include executable portions further configured to cause at least one processor to generate, for each of a plurality of provider entities, a compliance profile data object including a plurality of compliance scores for the provider entity with respect to the plurality of service need conditions. Generating the compliance profile data object for a particular provider entity includes: for each given service need condition of the plurality of service need conditions: (i) retrieving one or more procedural record data objects each describing a treatment provided by the particular provider entity for the given service need condition, and (ii) determining a compliance score of the particular provider entity for the given service need condition using the one or more procedural record data objects and a subset of the plurality of guideline data objects that are associated with the given service need condition. Generating the compliance profile data object for the particular provider entity further includes determining the compliance profile data object based at least in part on each compliance score. The computer-readable program code portions include executable portions further configured to cause at least one processor to select a selected subset of the plurality of provider entities according to the compliance profile data object for each provider entity. The computer-readable program code portions include executable portions further configured to cause at least one processor to perform at least one automated recommendation-based action based at least in part on the selected subset.

In accordance with yet another aspect, an apparatus including a processor and at least one memory including computer program code is provided. In various embodiments, the at least one memory and the computer program code are configured to, with the processor, cause the apparatus to generate a plurality of guideline data objects for a plurality of service need conditions. The at least one memory and the computer program code are further configured to, with the processor, cause the apparatus to generate, for each of a plurality of provider entities, a compliance profile data object including a plurality of compliance scores for the provider entity with respect to the plurality of service need conditions. Generating the compliance profile data object for a particular provider entity includes: for each given service need condition of the plurality of service need conditions: (i) retrieving one or more procedural record data objects each describing a treatment provided by the particular provider entity for the given service need condition, and (ii) determining a compliance score of the particular provider entity for the given service need condition using the one or more procedural record data objects and a subset of the plurality of guideline data objects that are associated with the given service need condition. Generating the compliance profile data object for the particular provider entity further includes determining the compliance profile data object based at least in part on each compliance score. The at least one memory and the computer program code are further configured to, with the processor, cause the apparatus to select a selected subset of the plurality of provider entities according to the compliance profile data object for each provider entity. The at least one memory and the computer program code are further configured to, with the processor, cause the apparatus to perform at least one automated recommendation-based action based at least in part on the selected subset.

BRIEF DESCRIPTION OF THE DRAWINGS

Having thus described the invention in general terms, reference will now be made to the accompanying drawings, which are not necessarily drawn to scale.

Figure 1:
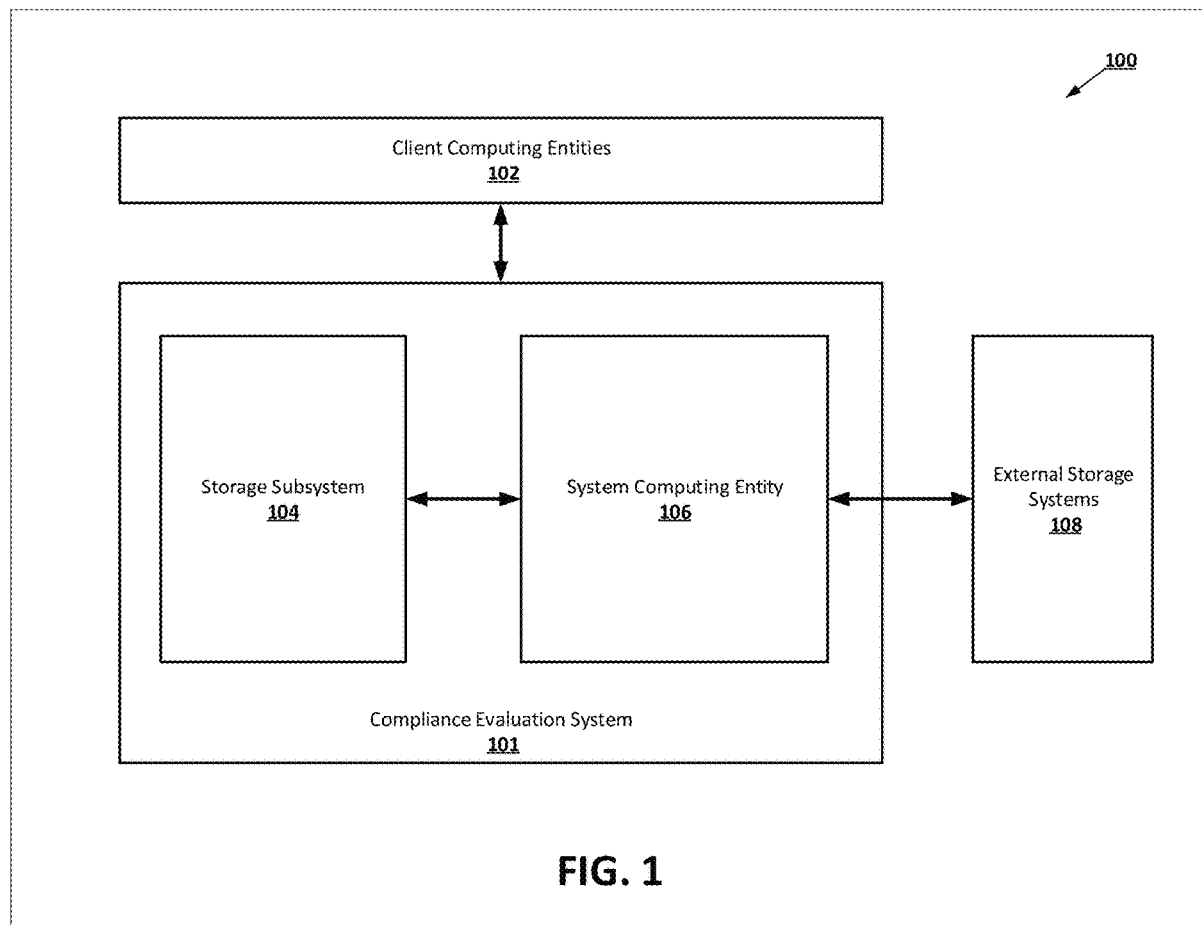

FIG. 1 provides an exemplary overview of an architecture that may be used to practice embodiments of the present disclosure.

Figure 2:
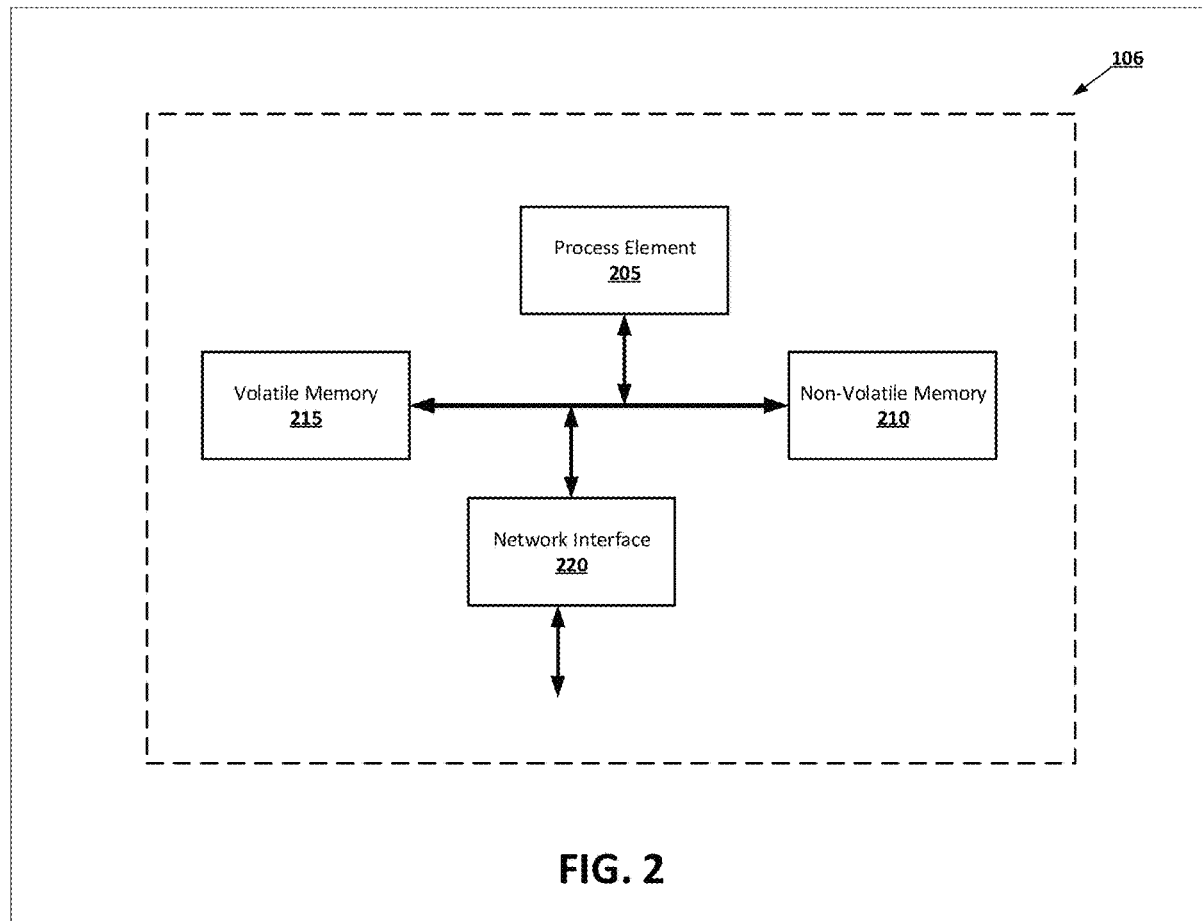

FIG. 2 provides a diagram of an example system computing entity, in accordance with some embodiments discussed herein.

Figure 3:
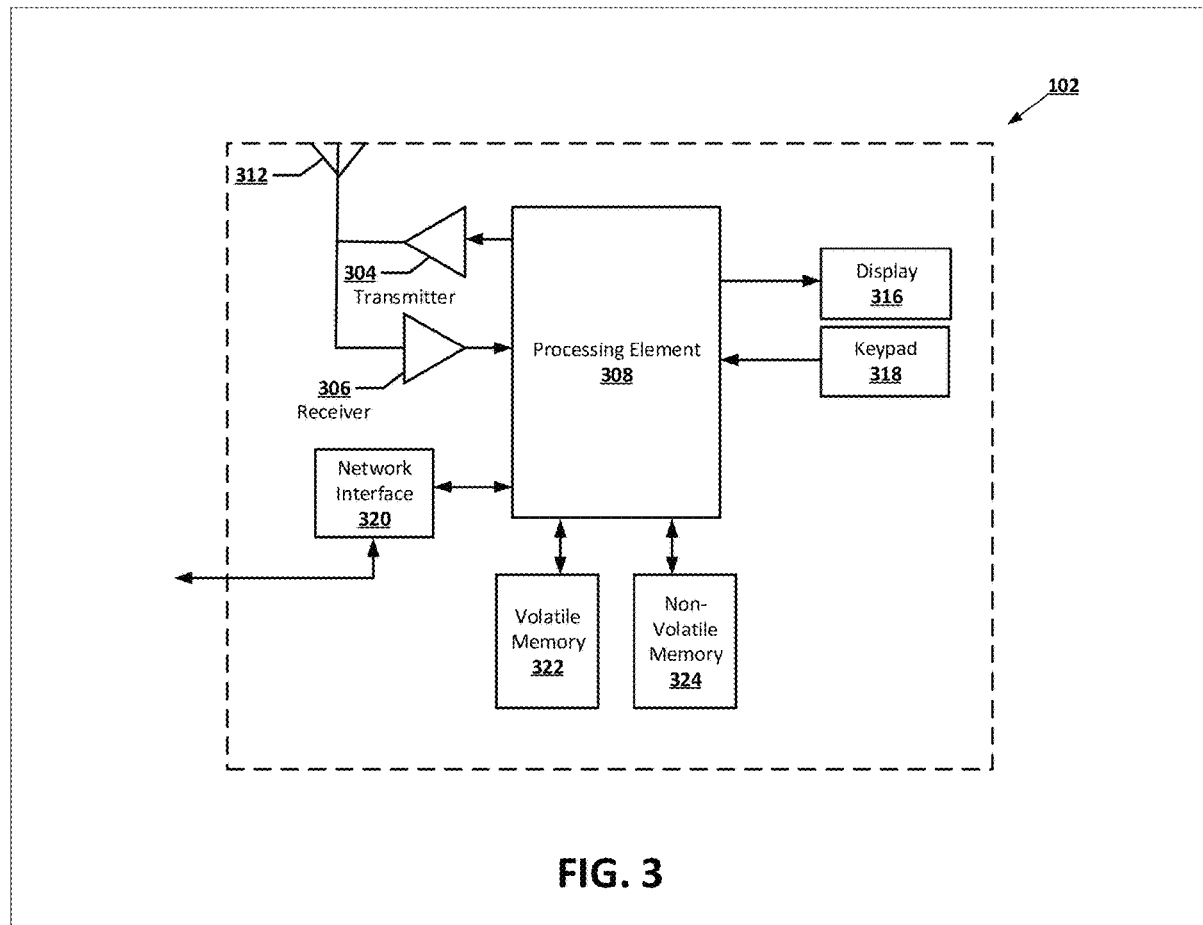

FIG. 3 provides a diagram of an example client computing entity, in accordance with some embodiments discussed herein.

Figure 4:
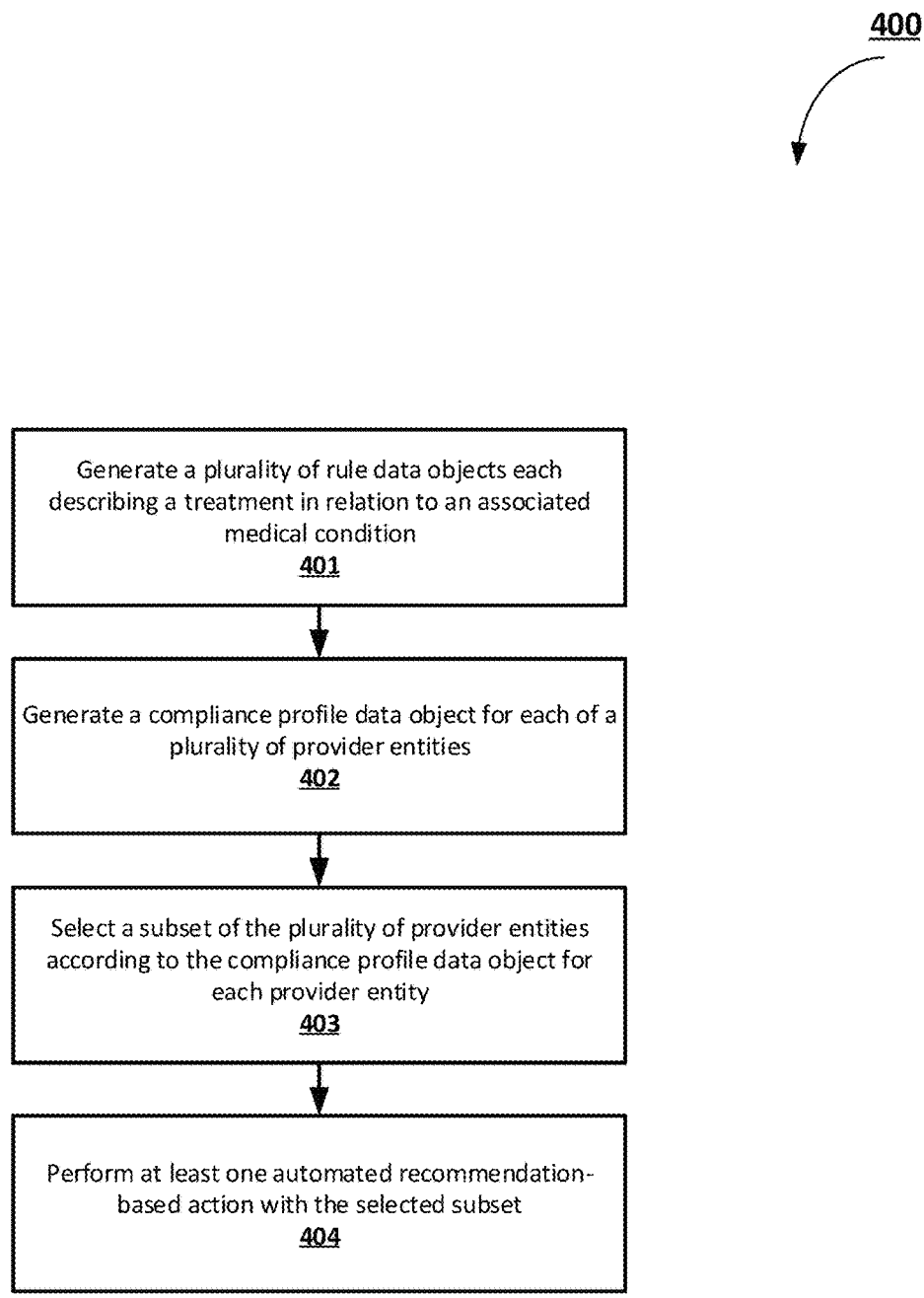

FIG. 4 provides a flowchart diagram of an example process for recommending healthcare providers for a patient at least according to provider compliance with treatment guidelines for service need conditions, in accordance with some embodiments discussed herein.

Figure 5:
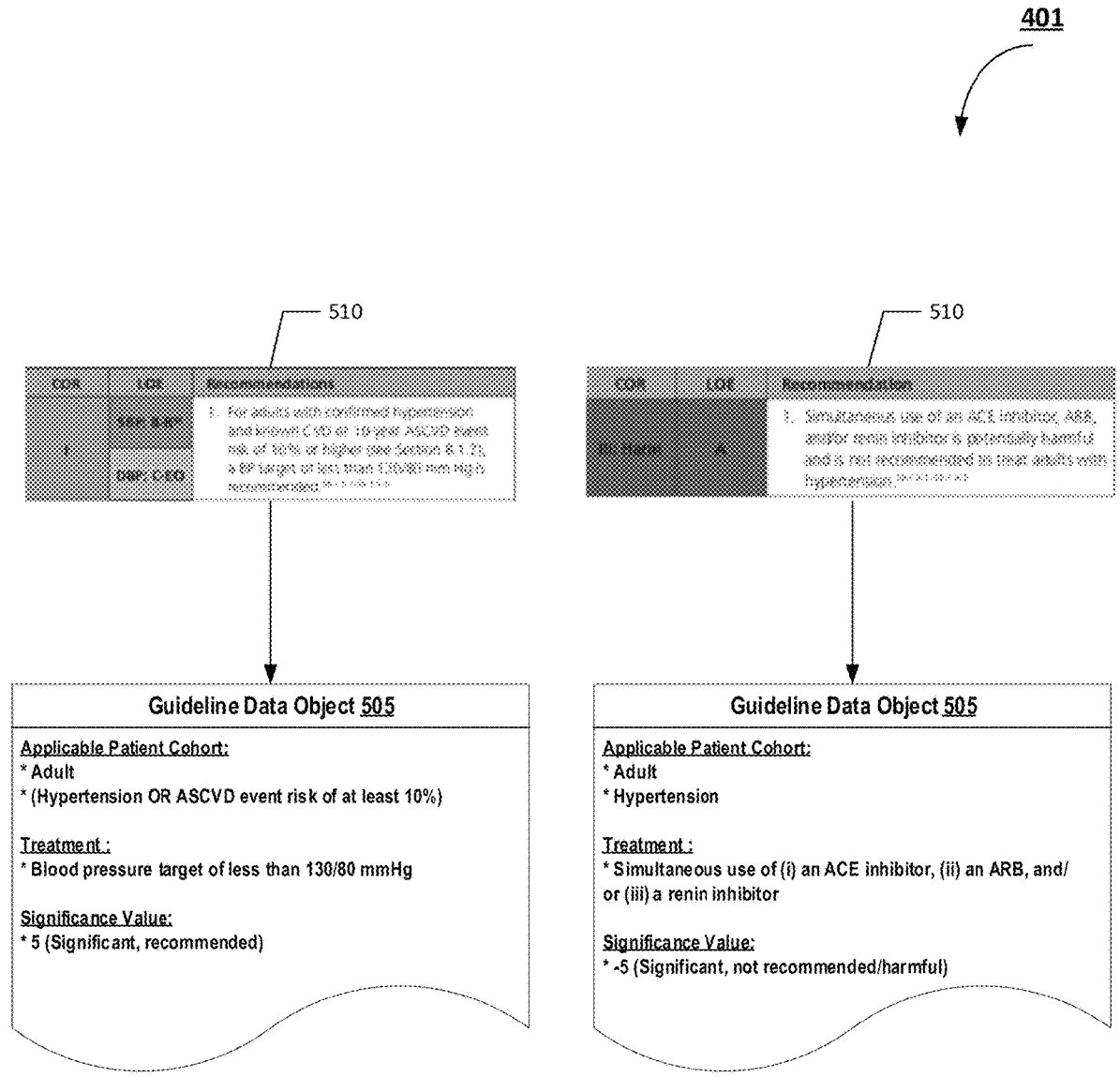

FIG. 5 illustrates example guideline data objects describing recommended treatments and generated for evaluation of healthcare providers, in accordance with some embodiments discussed herein.

Figure 6:
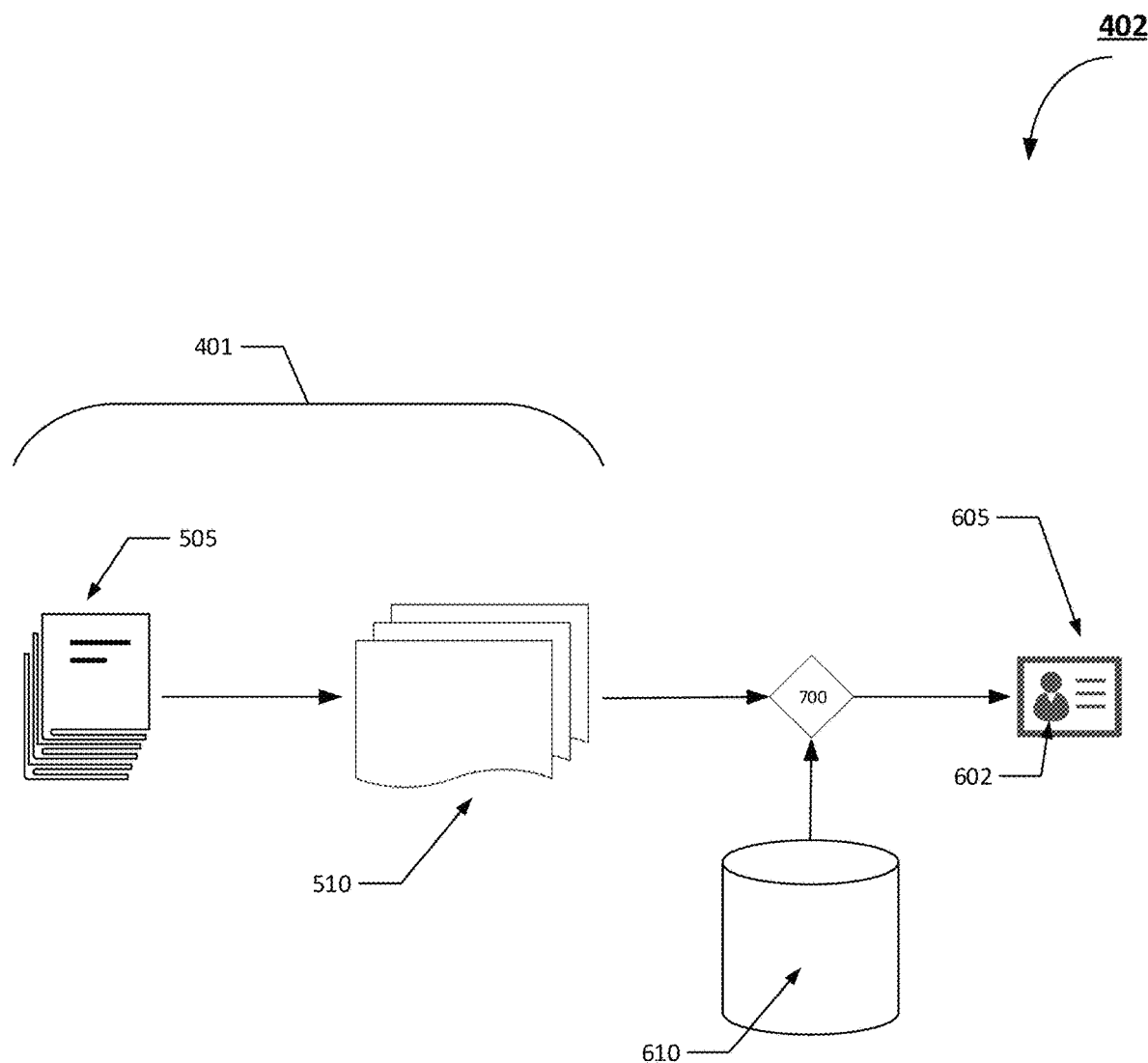

FIG. 6 provides a diagram describing the profiling of a provider entity according to the provider entity's compliance with recommended treatments, in accordance with some embodiments discussed herein.

Figure 7:
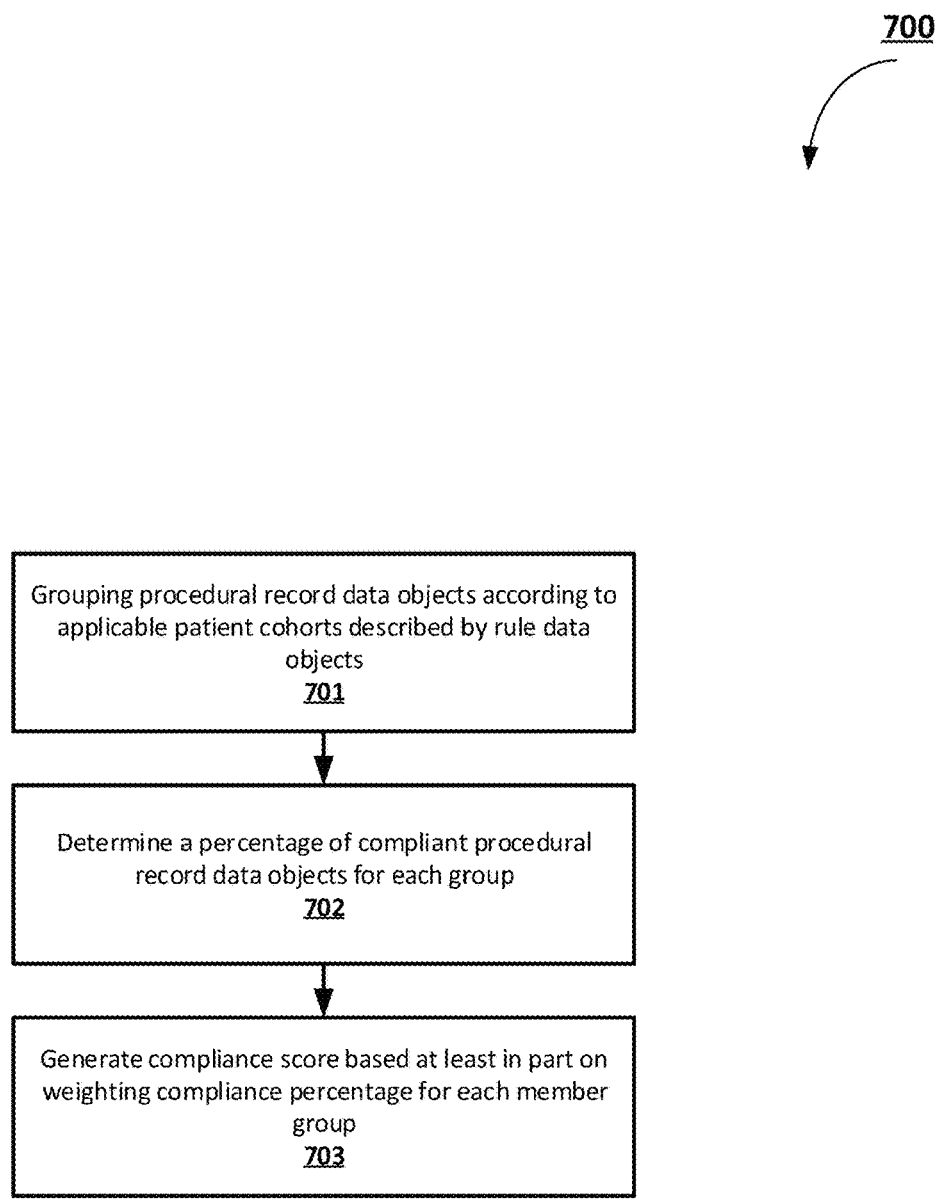

FIG. 7 provides a flowchart diagram of an example process for profiling a provider entity according to the provider entity's compliance with recommended treatments, in accordance with some embodiments discussed herein.

Figure 8:
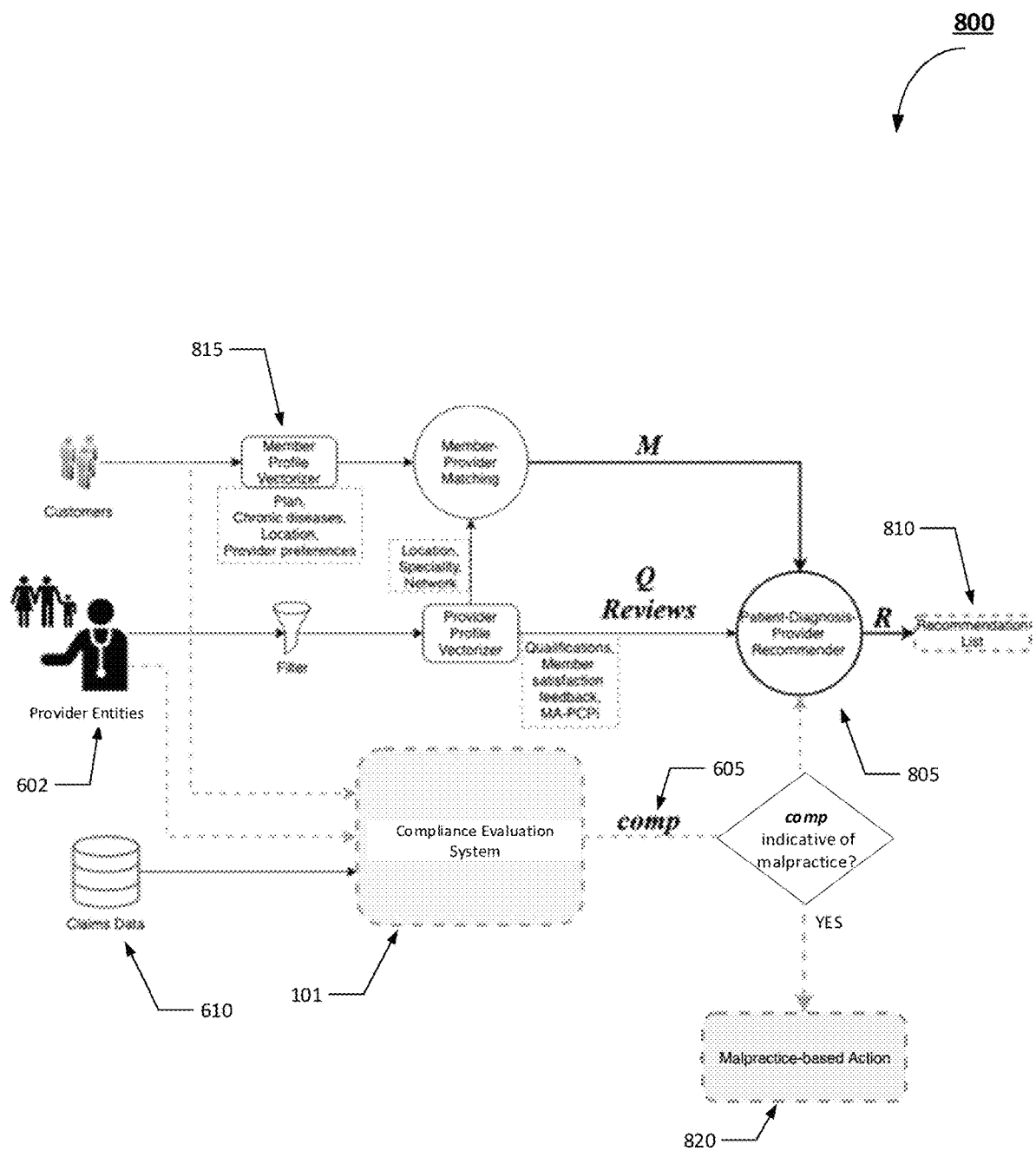

FIG. 8 illustrates an overview diagram of a provider recommendation system configured to recommend healthcare providers for a patient at least according to provider compliance with recommended treatments and procedures, in accordance with some embodiments discussed herein.

DETAILED DESCRIPTION

Various embodiments of the present disclosure now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present disclosure are described with reference to providing text-based summarizations of conversations, one of ordinary skill in the art will recognize that the disclosed concepts can be used in other summarization and/or text extraction applications.

I. OVERVIEW AND TECHNICAL IMPROVEMENTS

Various embodiments of the present disclosure address technical challenges related to improving computational efficiency, operational reliability, and operational throughput of predictive recommendation systems. By disclosing techniques for generating more effective recommendations, various embodiments of the present invention reduce the number of repeated queries by end-users to generate predictive recommendations. This in turn: (i) decreases the number of computational operations performed by processing units of predictive recommendation systems, thus increasing the computational efficiency of predictive recommendation systems, (ii) decreases the overall likelihood of system failure given a constant per-recommendation likelihood failure, thus increasing operational reliability of predictive recommendation systems, and (iii) increases the overall number of end-users that the predictive recommendation system can serve given a constant per-user query count, thus increasing the operational throughput of predictive recommendation systems. Accordingly, various embodiments of the present disclosure make important technical contributions to the field of predictive data analysis by improving computational efficiency, operational reliability, and operational throughput of predictive recommendation systems.

Various embodiments of the present disclosure address technical challenges related to recommendation of healthcare providers for a patient with respect to the treatment and procedures provided to the patient by the healthcare providers. In particular, various embodiments described herein are directed to recommending healthcare providers based at least in part on provider compliance with or adherence to established guidelines for medical treatment for various service need conditions. Evaluation and consideration of provider compliance provides additional depth and dimension to healthcare provider recommendation and improves a predicted match quality and accuracy between a patient and a recommended healthcare provider. For instance, various embodiments of the present disclosure may use provider compliance with other factors including provider demographics, patient demographics, patient-provider distance, provider qualifications, provider cost, and/or the like to provide a holistically-based recommendation of healthcare providers for a patient.

In various embodiments, evaluation of provider compliance involves extraction of established clinical guidelines for service need condition treatments. Further, historical data describing treatment and procedures provided by provider entities may be retrieved, such historical data including healthcare claims data submitted to a medical insurance entity, electronic medical records associated with patients, medical facility records and logs, and/or the like. The treatment and procedures provided by provider entities may then be compared with the extracted clinical guidelines. Specifically, such clinical guidelines identify applicable patient cohorts to whom the described treatments apply (e.g., are recommended for, are not recommended for), and the comparison may be done on a cohort basis to determine provider compliance. Overall then, a provider entity may be profiled with compliance for certain service need conditions.

In some example embodiments, evaluation of provider compliance enables provider malpractice to be detected and further enables automated malpractice-based actions to be performed. Example malpractice-based actions may include generating and providing a malpractice report to a governing entity, automatically notifying the provider entity, automatically providing clinical guidelines resources to the provider entity, removal of the provider entity from service networks, and/or the like. Generally, it may be appreciated that provider compliance to clinical guidelines for treatment of service need conditions can be used as an evaluation metric for provider entities and can be integrated with other provider-specific features to provide a holistic characterization of providers for applications other than recommendation.

Various embodiments of the present disclosure involve selection of provider entities for recommendation for a patient at least according to the determined provider compliance of each provider entity. In various embodiments, the patient is profiled according to the patient's current diagnoses as well as a predicted risk of the patient to develop certain service need conditions in the near future. This patient profiling enables provider entities to be recommended that are compliant with clinical guidelines with respect to the exact service need conditions for which the patient needs or may need treatment. That is, various provider compliance profiles may be weighted according to the needs (e.g., predicted needs) of the patient, and their associated provider entities may be subsequently ranked for recommendation to the patient.

Therefore, various embodiments of the present disclosure provide various technical advantages and technical solutions through recommending healthcare providers at least according to provider compliance with established clinical guidelines for medical treatment. Recommendation quality and accuracy through provider compliance and incorporation thereof with other features reduces overall system load and user interaction through improvement to user satisfaction. For instance, improved recommendation of healthcare providers reduces an amount of user inquiries regarding alternative providers received by a provider recommendation system, as well as reduces a total amount of data processing, transmission, and communication prompted from users requesting transitions between different providers frequently.

II. EXEMPLARY DEFINITIONS OF CERTAIN TERMS

The term "guideline data object" may refer to a data entity configured to describe a comprehensive clinical guideline related to a service need condition. Specifically, a guideline data object may describe guidelines with different levels of recommendation or significance. For example, a first guideline data object may describe a guideline for administration of a drug highly recommended to treat a condition or may describe a guideline to not administer a drug harmful or detrimental to treating a condition. Thus, a guideline data object can describe a positively recommended treatment or negatively recommended treatment. Compliance and adherence by provider entities to guideline data objects (e.g., to guidelines described by the guideline data objects) is evaluated in various embodiments described herein for recommendation of provider entities for a patient.

Guideline data objects may be extracted (e.g., via natural language processing) from various reference datasets, such as medical textbooks or clinical practice resources, and/or may be generated manually (e.g., via user input). In various embodiments, a guideline data object comprises (i) an applicable patient cohort, (ii) an indication of a treatment, a procedure, and/or the like, and (iii) a significance value, and the guideline data object is associated with a particular service need condition. The applicable patient cohort describes a subset or a subpopulation of a population of patients that are at risk for, diagnosed with, and/or having the particular service need condition to whom the treatment is recommended (or not recommended). For example, the applicable patient cohort may be a data entity including a list of patient identifiers, a set of physical or medical characteristics, and/or the like. The guideline data object may indicate or identify the treatment or procedure using unique identifiers assigned to various treatments or procedures, including Current Procedural Terminology (CPT) codes, National Drug Code (NDC) codes, Anatomical Therapeutic Chemical (ATC) codes, and/or the like. The significance value provides a measure of the extent to which the treatment is positively or negatively recommended. In some examples, the significance value is bounded and discrete (e.g., integers between −5 and 5). Thus, a guideline data object provides a comprehensive description of a treatment guideline with regard to a particular service need condition. In various embodiments, a guideline data object is a vector, a matrix, an array, a data structure, embeddings, a dataset, and/or the like.

The term "provider entity" may describe an entity providing healthcare services to patients. For example, a provider entity may be a healthcare provider, physician, doctor, and/or the like. In another example, a provider entity may be a group of providers, a healthcare facility or hospital employing a plurality of providers, an organization of providers, and/or the like. In various embodiments, a provider entity is evaluated for compliance or adherence to guideline data objects for various service need conditions. Specifically, past performance, including procedures performed, of a provider entity (or providers thereof) is compared to guideline data objects on a service need condition basis. Such compliance of a provider entity is described by a compliance profile data object associated with the provider entity. In some examples, a provider entity has demographic information, such as age, gender, address, degree, specialty, and/or the like. A provider entity is associated with an identifier, a unique identifying value or code, a unique token (e.g., a globally unique identifier or GUID, a universally unique identifier or UIUD), and/or the like.

The term "procedural record data object" may refer to a data entity that is configured to generally describe a treatment, procedure, and/or the like provided by a provider entity. In some example embodiments, a procedural record data object may be and/or may be generated from (e.g., extracted from) a healthcare claim, an electronic medical record (EMR), and/or the like. In describing a treatment or procedure provided by the provider entity, a procedural record data object may comprise an indication or a unique identifier associated with the treatment or procedure, such as a CPT code, a NDC code, and/or the like. A procedural record data object may additionally comprise an indication of one or more service need conditions prompting the provided treatment or procedure, such as a diagnosis code (e.g., an International Classification of Diseases or ICD code). A procedural record data object may further identify and/or describe the patient for whom the treatment or procedure was provided, as well as other data such as a timestamp, a location, a cost, and/or the like. In various embodiments, a procedural record data object is a vector, a matrix, an array, a data structure, embeddings, a dataset, and/or the like.

The term "compliance profile data object" may refer to a data entity configured to describe compliance or adherence to established guidelines for healthcare treatment by a provider entity. A compliance profile data object corresponds to a provider entity. In various embodiments, a compliance profile data object for a provider entity is generated using procedural record data objects describing treatments or procedures provided by the provider entity prompted by particular service need conditions and using guideline data objects describing recommended (or not recommended) treatments for the same particular service need conditions. In various embodiments, a compliance profile data object for a provider entity comprises one or more compliance scores that individually describe compliance with respect to a service need condition. In various embodiments, a compliance profile data object is a vector, a matrix, an array, a data structure, embeddings, a dataset, and/or the like. For example, the compliance profile data object is a vector of compliance scores, in an example embodiment.

The term "compliance score" may refer to a data entity configured to describe compliance of a provider entity with respect to a specific service need condition. In accordance with preceding description, compliance scores can be determined and generated using procedural record data objects describing treatments or procedures provided by the provider entity in order to treat the specific service need condition and using guideline data objects describing positively and/or negatively recommended guidelines for treating the specific service need condition. Generally, a compliance score is based at least in part on a percentage of patients for which the provider entity provided treatments or procedures that comply with the guideline data objects. In various embodiments, the compliance score may be a scalar value, embeddings, and/or the like.

The term "patient condition profile data object" may refer to a data entity configured to describe a patient's risk or likelihood of having certain service need conditions. In various embodiments, the patient condition profile data object comprises a deterministic flag and a stochastic value for each of a set of service need conditions. The deterministic flag may indicate whether or not the patient has been diagnosed with an associated service need condition; for example, the deterministic flag may be binary in nature. The stochastic value may describe a predicted risk of the patient having the associated service need condition at present or developing the associated service need condition in the near future. In some example embodiments, the stochastic value is generated using historical data (e.g., procedural record data objects) for the patient and a risk prediction machine learning model. For example, the risk prediction machine learning model is configured (e.g., trained) to output a probabilistic value of the associated service need condition being present or being developed based at least in part on the historical data for the patient. In various embodiments, a patient condition profile data object is a vector, a matrix, an array, a data structure, embeddings, a dataset, and/or the like.

III. COMPUTER PROGRAM PRODUCTS, METHODS, AND COMPUTING ENTITIES

Embodiments of the present disclosure may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of an apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example system architecture 100 for evaluating compliance of a provider entity with clinical guidelines for treatment of service need conditions. In various embodiments, the system architecture 100 is further configured for recommendation of provider entities at least according to an evaluated or determined compliance of the provider entities with clinical guidelines for treatment of service need conditions. The system architecture 100 may be used at least to generate guideline data objects describing clinically recommended (or non-recommended) treatments from reference datasets, to generate compliance profile data objects for each of a plurality of provider entities, to select certain provider entities for recommended based at least in part on associated compliance profile data objects, and to perform various recommendation-based actions.

The system architecture 100 includes a compliance evaluation system 101 configured to evaluate compliance for provider entities, such as by at least generating a compliance profile data objects for each of a plurality of provider entities. In various embodiments, the compliance evaluation system 101 is further configured for selection of provider entities for recommendation for a patient based at least in part on various criteria including provider compliance. Alternatively, in other example embodiments, the system architecture 100 includes a provider recommendation system that is communicatively coupled with the compliance evaluation system 101, such as to receive compliance profile data objects for provider entities for consideration during selection of provider entities for recommendation.

In various embodiments, the compliance evaluation system 101 is configured to extract and process text from clinical guideline resources and reference datasets in order to generate guideline data objects for use in evaluating compliance of provider entities. In various embodiments, the compliance evaluation system 101 is further configured to receive and/or retrieve procedural record data objects (e.g., claims data, EMR data) to discover past practices of provider entities from which compliance is determined. As illustrated, the system architecture includes one or more external storage systems 108, which may include various databases storing said clinical guideline resources and reference datasets and procedural record data objects. For example, at least one of the external storage systems 108 is a healthcare claims database. In various embodiments, the compliance evaluation system 101 is configured to generate (e.g., and output) compliance profile data objects describing provider compliance across service need conditions for a plurality of provider entities.

In some embodiments, the compliance evaluation system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like). In various embodiments, the compliance evaluation system 101 comprises an application programming interface (API) through which API queries for compliance evaluation may be received and through which compliance profile data objects may be provided in API responses. Specifically, API queries may originate from client computing entities 102 interested in provider compliance for a plurality of provider entities, and the API responses that include compliance profile data objects may be provided to the same client computing entities 102. In some example embodiments, a client computing entity 102 may be and/or may comprise a provider recommendation system, and as such, may request and receive compliance profile data objects for provider entities from the compliance evaluation system 101.

The compliance evaluation system 101 may include a system computing entity 106 and a storage subsystem 104. The system computing entity 106 may be configured to perform various operations described herein to generate guideline data objects, obtain procedural record data objects associated with provider entities, and generate compliance profile data objects for the provider entities, as well as various automated actions including providing compliance profile data objects to a client computing entity 102 and malpractice-based actions. In various embodiments, the system computing entity 106 is a cloud-based computing system and comprises one or more computing devices each configured to share and allocate computer processing resources and data The storage subsystem 104 may be configured to store certain data for evaluation of provider compliance and/or for recommendation of provider entities at least according to provider compliance. For instance, in example embodiments, the storage subsystem 104 stores compliance profile data objects each corresponding to a provider entity and is configured to update such stored compliance profile data objects if necessary. In some example embodiments, the storage subsystem 104 is configured to store guideline data objects generated by the system computing entity 106, and in an example embodiment, the storage subsystem 104 stores various clinical and textual guidelines for treatment of service need conditions from which the guideline data objects may be generated. In some example embodiments, the storage subsystem 104 is configured to store procedural record data objects that describe treatments provided by provider entities.

The storage subsystem 104 may include one or more storage units, such as multiple distributed storage units that are connected through a computer network. Each storage unit in the storage subsystem 104 may store at least one of one or more data assets and/or one or more data about the computed properties of one or more data assets. Moreover, each storage unit in the storage subsystem 104 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Computing Entities

In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

FIG. 2 provides a schematic of a system computing entity 106, according to one embodiment of the present disclosure. As shown in FIG. 2, in one embodiment, the system computing entity 106 may include, or be in communication with, one or more processing elements 205 (also referred to as processors, processing circuitry, and/or similar terms used herein interchangeably) that communicate with other elements within the system computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the system computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media 210 may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the system computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media 215 may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the system computing entity 106 with the assistance of the processing element 205 and operating system.

As indicated, in one embodiment, the system computing entity 106 may also include one or more network interfaces 220 for communicating with various computing entities (e.g., one or more other system computing entities 106, one or more client computing entities 102), such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the system computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the system computing entity 106 may include, or be in communication with, one or more input elements, such as a keyboard input, a mouse input, a touch screen/display input, motion input, movement input, audio input, pointing device input, joystick input, keypad input, and/or the like. The system computing entity 106 may also include, or be in communication with, one or more output elements (not shown), such as audio output, video output, screen/display output, motion output, movement output, and/or the like.

FIG. 3 provides a schematic of an example client computing entity 102 that may be used in conjunction with embodiments of the present disclosure. Client computing entities 102 can be operated by various parties, and the system architecture 100 may include one or more client computing entities 102. Within the system architecture 100, client computing entities 102 may be operated to request evaluation of provider compliance for certain provider entities and may receive provider compliance data objects for the certain provider entities. A client computing entity 102 may identify certain provider entities, such as via unique identifiers (e.g., National Provider Identifier number), for compliance evaluation. In such example instances, some client computing entities 102 may be operated by and/or associated with healthcare and insurance entities having an interest in provider performance and evaluation of providers (e.g., for service network management), provider evaluation and/or governing entities (e.g., certification boards) that may be particularly interested in provider malpractice, and/or the like.

Similarly, client computing entities 102 may be operated to request recommendation of provider entities and may receive a set of provider entities (e.g., a set of NPI numbers identifying recommended provider entities) that are recommended based at least in part on various criteria including provider compliance. The request for provider recommendation originating from a client computing entity 102 may identify a group of provider entities from which recommendation is sought and/or may identify various other criteria to be evaluated in said recommendation. In various example embodiment, client computing entities 102 may be operated by and/or associated with patients seeking a services and treatment from a provider entity, emergency services (e.g., an ambulance) seeking a provider entity for delivery and transport of a patient, and/or the like.

As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the system computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the system computing entity 106 via a network interface 320.

Via these communication standards and protocols, the client computing entity 102 can communicate with various other entities (e.g., system computing entities 106, storage subsystem 104) using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like.

Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the system computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the system computing entity 106, various other computing entities, and/or a storage subsystem 104.

In another embodiment, the client computing entity 102 may include one or more components or functionality that are the same or similar to those of the system computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

As described below, various embodiments of the present invention address technical challenges related to improving computational efficiency, operational reliability, and operational throughput of predictive recommendation systems. By disclosing techniques for generating more effective recommendations, various embodiments of the present invention reduce the number of repeated queries by end-users to generate predictive recommendations. This in turn: (i) decreases the number of computational operations performed by processing units of predictive recommendation systems, thus increasing the computational efficiency of predictive recommendation systems, (ii) decreases the overall likelihood of system failure given a constant per-recommendation likelihood failure, thus increasing operational reliability of predictive recommendation systems, and (iii) increases the overall number of end-users that the predictive recommendation system can serve given a constant per-user query count, thus increasing the operational throughput of predictive recommendation systems. Accordingly, various embodiments of the present invention make important technical contributions to the field of predictive data analysis by improving computational efficiency, operational reliability, and operational throughput of predictive recommendation systems.

Various embodiments of the present disclosure address technical challenges related to recommendation of provider entities at least according to compliance of treatments provided by the provider entities with established clinical guidelines described by guideline data objects. In particular, past treatments provided by provider entities are referenced against guideline data objects to determine provider compliance, and provider compliance is profiled across different service need conditions. In various embodiments, provider entities are recommended to a patient specifically based at least in part on their compliance with respect to service need conditions that are relevant to the patient. By improving upon fidelity, dimensionality, and accuracy of provider recommendations, various embodiments address technical challenges generally related to healthcare provider recommendations such as by reducing overall system load and user interaction. For instance, improved recommendation of healthcare providers reduces an amount of user inquiries regarding alternative providers received by a system, as well as reduces a total amount of data processing, transmission, and communication prompted from users requesting transitions between different providers frequently.

FIG. 4 provides a flowchart diagram of an example process 400 for recommending provider entities for a patient at least according to provider compliance. In various embodiments, the system computing entity 106 comprises means, such as the processing elements 205, memory media 210, 215, network interface 220, and/or the like, for recommending provider entities for a patient at least according to provider compliance and for performing steps/operations of process 400. In various embodiments, the client computing entity 102 also comprises means, such as processing elements 308, memories 322, 324, network interface 320, and/or the like, for recommending provider entities for a patient at least according to provider compliance and for performing steps/operations of process 400.

Process 400 comprises step/operation 401, at which a plurality of guideline data objects are generated. In particular, the plurality of guideline data objects are generated from one or more reference datasets, which may be stored in an external storage system 108. In various embodiments, the plurality of guideline data objects may be generated manually by an expert such as a medical professional. For example, an expert user or operator (e.g., a user with a special designation and/or unique credentials) may provide user input to specify guideline data objects. This user input may specify guideline data objects in their entirety, may specify guideline data objects based at least in part on the one or more reference datasets (e.g., highlighting and selecting certain portions of a reference dataset), and/or the like. In various other embodiments, the plurality of guideline data objects may be generated automatically based at least in part on natural language processing of various textual medical resources (e.g., textbooks, journal papers, convention presentations) and/or analysis of at least semi-structured guideline data.

As discussed, a guideline data object is configured to describe an established clinical guideline with respect to treatment of a service need condition, and as such, the plurality of guideline data objects may be associated with certain service need conditions. Specifically, each guideline data object identifies and is associated with a service need condition. Generally, a guideline data object may describe an established clinical guideline for a recommended treatment for the associated service need condition or may describe an established clinical guideline for harmful or non-recommended actions in treatment of the associated service need condition.

In describing a clinical guideline, a guideline data object is generated to include comprehensive information and parameters of the clinical guideline. In particular, a rule data comprises an applicable patient cohort, an indication of one or more treatments, procedures, and/or the like, and a significance value. In various embodiments, the applicable patient cohort of the guideline data object identifies certain patients for whom the clinical guideline is applicable. The applicable patient cohort may identify patients based at least in part on explicitly describing certain physical or medical characteristics or criteria (e.g., biometrics, diagnosis history). In some instances, the applicable patient cohort may identify patients by demographic criteria (e.g., age ranges, location).

Meanwhile, the indication of one or more treatments, procedures, and/or the like of a guideline data object is configured to uniquely identify a recommended or non-recommended described by the clinical guideline. For instance, the guideline data object may comprise one or more CPT codes describing certain procedures (e.g., surgeries, operations, management of vitals) and/or one or more NDC codes describing certain drugs that are recommended or non-recommended by the clinical guideline.

In various embodiments, the significance value of the guideline data object describes both whether the clinical guideline describes a recommended action or a non-recommended and the degree to which the action is recommended or cautioned. For example, the significance value may be an integer value bounded by a positive number and a negative number (e.g., 5 to −5), with negative integer values indicating harmfulness or non-recommendation. In various embodiments, the guideline data object includes other various parameters or data to describe the clinical guideline. For example, a guideline data object may identify a reference dataset from which the clinical guideline originates.

FIG. 5 illustrates example generation of guideline data objects 505 from reference data 510. As discussed, the reference data 510 may be stored in an external storage system 108 from which it is accessed for generation of guideline data objects 505 (e.g., by a system computing entity 106, by a client computing entity 102). In alternative example embodiments, reference data 510 may be stored in a storage subsystem 104 of a compliance evaluation system 101, in memory 210, 215 of a system computing entity 106, and/or the like. In some embodiments, the reference data 510 is in the form of unstructured or semi-structured text. For instance, an illustrated reference data 510 of the illustrated embodiment recites as a recommendation: "For adults with confirmed hypertension and known CVD or 10-year ASCVD event risk of 10% of higher [ . . . ], a BP target of less than 130/80 mm Hg is recommended." The reference data 510 generally may include additional information from which components of a guideline data object may be generated, such as an explicit description of a significance value.

As shown in FIG. 5, a guideline data object 505 may be generated based at least in part on processing and analysis of reference data 510. In the illustrated embodiment, an applicable patient cohort for the guideline data object 505 is generated based at least in part on the criteria of "adult" and the criteria of "confirmed hypertension and known CVD or 10-year ASCVD event risk of 10% or higher". As will be understood then, an applicable patient cohort may include binary criteria (e.g., adult vs. non-adult, existing diagnosis of hypertension vs. no diagnosis of hypertension) and/or quantitative criteria, such as predicted risk threshold for a service need condition. In various embodiments, the guideline data object 505 comprises one or more identifiers configured to describe diagnosis of a service need condition (e.g., an ICD code) and an identifier may be associated with a predicted risk threshold. In some example, the applicable patient cohort describes a temporally-based criteria, for example, to bias recent events experienced by applicable patients. For example, a guideline data object 505 may comprise an applicable patient cohort identifying patients being diagnosed with a service need condition within the last two years while excluding patients diagnosed with the service need condition more than two years ago. Generally, a guideline data object 505 comprises an applicable patient cohort identifying patients based at least in part on a single criteria or a combination of criteria (e.g., composite criteria).

Such criteria may be generated based at least in part on processing and analysis of the reference data 510. In various embodiments, a classification machine learning model, a recurrent neural network (RNN) machine learning model, a long short-term memory (LSTM)-based machine learning model, and/or the like are configured and used to parse tokens (e.g., each word) of text of the reference data 510 and are configured to at least identify and output criteria related to an applicable patient cohort. In some example embodiment, the applicable patient cohort of a guideline data object 505 is manually generated and specified by a user based at least in part on manual analysis of the reference data 510. The manual analysis of the reference data 510 may be at least enabled in various embodiments by providing the reference data 510 for display and by enabling a user to select portions of the reference data 510 as an applicable patient cohort (e.g., via user input). In some example embodiments, such user selections of portions of reference data 510 may be used to train and configured the aforementioned machine learning models to identify significant portions of reference data 510 as an applicable patient cohort.

As also illustrated in FIG. 5, a guideline data object 505 comprises an indication of a treatment generated according to the reference data 510. In the illustrated embodiment, for example, the treatment indicated by the guideline data object 505 is the maintenance of blood pressure below 130/80 mm Hg. As also illustrated in FIG. 5, the treatment indicated by a guideline data object 505 may be one or more drugs, pharmaceuticals, compounds, solutions, nutrients, and/or the like recommended or not recommended for administration to a patient. In further example instances, the treatment indicated by a guideline data object 505 may be a procedure, an operation, a surgery, a routine, and/or the like.

Although not explicitly illustrated, a guideline data object 505 indicates such treatments described by the reference data 510 using unique identifiers associated with different treatments, drugs, routines, and/or the like. For instance, a renin inhibitor may be described by a guideline data object 505 via one or more NDC codes for renin inhibitors, such as NDC code 70839-150-30 for 150 mg tablet Tekturna. Likewise, a procedure may be described by a guideline data object 505 via an associated CPT code. Identification of the treatment described by the reference data 510 may be supplemented with additional information such as dosage amounts, administration time span, and/or the like.

Various embodiments may generate the indication of a treatment of a guideline data object 505 using a classification machine learning model, a RNN machine learning model, a LSTM-based machine learning model, and/or the like. In an example embodiment, a significance-based machine learning model is configured to identify significant text within the reference data 510 that relates to a treatment, such as identify text near certain phrases including " . . . is recommended" or "use of . . . " that may suggest description of a treatment as in FIG. 5. The significance-based machine learning model may be configured to further classify identified descriptions of treatments and output a unique identifier such as an NDC code, an ATC code, a CPT code, and/or the like.

In the illustrated embodiment of FIG. 5, the significance value of a guideline data object 505 is generated from the reference data 510, and in some examples, the reference data 510 is at least semi-structured such that the significance value is substantially described. As discussed, the significance value may at least indicate whether the treatment described is recommended or not recommended, such as by using positive or negative values, and the significance value may also be generated based at least in part on natural language processing (e.g., sentiment analysis) of the reference data 510. For example, an attention-based machine learning model may be configured to identify text in the reference data 510, such as "highly recommended", "significantly recommended", "not recommended", "extremely harmful", "very dangerous", "mildly recommended", and/or the like, and to output a significance value based at least in part on the identified text.

Thus, as described, various machine learning models configured to generate an applicable patient cohort based at least in part on identifying patient criteria, to generate an indication of a treatment based at least in part on classification of key textual portions of reference data 510 with unique identifiers (e.g., an NDC code, a CPT code), and to generate a significance value based at least in part on attention to significance-describing textual portions of reference data 510, may each be used (e.g., in various combinations) to generate guideline data objects 505. In some example embodiments, automatically generated guideline data objects 505 may be manually verified and/or modified by an expert such as a medical professional. In various embodiments, generated guideline data objects may be stored in an accessible location, such as in memory 210, 215, storage subsystem 104, an external storage system 108, and/or the like.

In various embodiments, certain guideline data objects for a given service need condition may be relevant for similar patient cohorts and/or may describe similar treatments for different patient cohorts. In such embodiments, repeated applicable patient cohorts of guideline data objects 505 as well as repeated treatment indications can be extracted from the plurality of guideline data objects 505, and a cohort-treatment matrix for the given service need condition can be generated. The cohort-treatment matrix can be configured to clearly describe different treatments applicable to a given cohort as well as describe different cohorts to which a given treatment is applicable. Thus, in various embodiments, guideline data objects 505 for a given service need condition may be aggregated in some form, such as in a cohort-treatment matrix, to provide relationships between patient cohorts and treatments.

Returning to FIG. 4, process 400 includes step/operation 402, at which a compliance profile data object is generated for each of a plurality of provider entities. In various embodiments, the compliance profile data object for a provider entity is generated using at least some of the plurality of guideline data objects 505; that is, the compliance profile data object describes compliance of the provider entity in accordance with the guideline data objects 505. Generally, a compliance profile data object is generated to comprise one or more compliance scores individually corresponding to a service need condition, and thus, the compliance of a provider entity is profiled across different service need conditions.

FIG. 6 provides a diagram illustrating example generation of a compliance profile data object 605 for a provider entity 602. As illustrated in FIG. 6, generation of a compliance profile data object 605 is based at least in part on referencing guideline data objects 505, such as guideline data objects 505 generated from reference data 510 in accordance with step/operation 401. Thus, generation of compliance profile data objects 605 may be dependent on guideline data objects 505. FIG. 6 further illustrates that a compliance profile data object 605 for a provider entity 602 is generated based at least in part on a comparison or reference of procedural record data objects 610 associated with the provider entity 602 with the guideline data objects 505. The procedural record data objects 610 may be and/or may comprise healthcare claims data and/or electronic medical record data and generally may describe treatments provided by the provider entity 602 for a patient. In doing so, procedural record data objects 610 may comprise various information such as a unique identifier for the patient (e.g., an account number, a Social Security number, a date of birth), a timestamp, a location, unique identifiers associated with the treatment(s) provided (e.g., CPT codes, NDC codes, ATC codes), and/or the like. The procedural record data objects 610 may further include biometric and vital information of the patients being treated, physical characteristics, diagnoses of the patient by the provider entity 602, and/or the like.

As previously discussed, the compliance profile data object 605 comprises a plurality of compliance scores each corresponding to a service need condition, and FIG. 7 illustrates an example process 700 for generating a compliance score for a provider entity 602 with respect to a given service need condition using procedural record data objects 610 and guideline data objects 505. In various embodiments, the system computing entity 106 comprises means, such as the processing elements 205, memory media 210, 215, network interface 220, and/or the like, for generating a compliance score for a provider entity 602 with respect to a given service need condition and for performing steps/operations of process 700. In various embodiments, the client computing entity 102 also comprises means, such as processing elements 308, memories 322, 324, network interface 320, and/or the like, for generating a compliance score for a provider entity 602 with respect to a given service need condition and for performing steps/operations of process 400.

Process 700 comprises step/operation 701 for grouping procedural record data object 610 associated with the provider entity 602 according to applicable patient cohorts described by guideline data objects 505 associated with the given service need condition. It may be understood then that, in some example instances, a subset of the plurality of guideline data objects 505 is associated with the given service need condition and are accordingly used for grouping procedural record data objects 610 and generating the compliance score with respect to the given service need condition. In various embodiments, procedural record data objects 610 are grouped according a cohort-treatment matrix configured to describe the patient cohorts spanned by the guideline data objects 505 associated with the given service need condition. In various embodiments then, the guideline data objects 505 associated with the given service need condition are associated with some number of distinct or unique patient cohorts (e.g., a distinct or unique combination of patient-specific criteria), and the procedural record data objects 610 are grouped according to the distinct or unique patient cohorts.

In various embodiments, patients serviced or treated by the provider entity 602 are grouped, such patients being identified by the procedural record data objects 610. That is, in various embodiments, a population of patients that have interacted with the provider entity 602 (e.g., as evidenced by the procedural record data objects 610 associated with the provider entity 602) are grouped based at least in part on their personal characteristics satisfying applicable patient cohorts of the guideline data objects 505 associated with the given service need condition. Personal characteristics, such as biometric data, past diagnoses, demographic information, and/or the like, of these patients are also evidenced by and extracted from the procedural record data objects 610. Thus, with step/operation 701, the procedural record data objects 610 and/or the patients that they describe are grouped based at least in part on the guideline data objects 505 associated with the given service need condition.

As illustrated in FIG. 7, process 700 further comprises step/operation 702, which involves determining a percentage for each group of compliant procedural record data objects 610 and/or of compliantly-serviced patients. Specifically, for a number of procedural record data objects 610 that are grouped together according to a specific guideline data object 505, each procedural record data object 610 is evaluated to determine whether the procedural record data object 610 describes a treatment or a procedure administered by the provider entity 602 that is substantially similar and/or the same as the treatment or procedure described by the guideline data object 505, or whether the procedural record data object 610 is compliant.

In various embodiments, this determination may be based at least in part on a comparison of CPT codes, NDC codes, ATC codes, and/or the like described by a procedural record data object 610 with CPT codes, NDC codes, ATC codes, and/or the like described by the guideline data object 505. In various embodiments, the determination of similarity may be based at least in part on a predicted or determined similarity value, such as a cosine similarity value, according to characterization of a treatment described by a procedural record data object 610 (e.g., via textual data) and the treatment described by the guideline data object 505. For instance, both treatments described by the procedural record data object 610 and the guideline data object 505 may be vectorized using a neural network machine learning model, an LSTM-based machine learning model, an attention-based machine learning model, and/or the like configured to vectorize or generally generate a representation of textual data, and the determination of whether the procedural record data object 610 describes a treatment substantially similar to and/or the same as the treatment described by the guideline data object 505 is based at least in part on matching or performing cosine similarity of the two resulting vectors or representations.

In various embodiments, the group of procedural record data objects 610 may be associated with more than one guideline data objects 505. For instance, as previously discussed, multiple guideline data objects 505 may describe different treatments for the same applicable patient cohort. In such example embodiments, it is determined whether each procedural record data object 610 describes a treatment substantially similar and/or the same with at least one treatment described by the more than one guideline data objects 505. Accordingly, if it is determined that a procedural record data object 610 describes a substantially similar and/or the same treatment as the treatment described by one or more guideline data objects 505 associated with the group to which the procedural record data object 610 belongs, then the procedural record data object 610 may be labelled as a compliant procedural record data object.

Similarly, in some other example embodiments, the percentage of compliantly-serviced or compliantly-treated patients in each group of patients is determined. In determining whether a patient has been compliantly serviced or treated by the provider entity 602, procedural record data objects 610 that identify and describe the patient are analyzed. In some example instances, a patient may be repeatedly treated by the provider entity 602, and as such, multiple procedural record data objects 610 may describe different treatments provided to the patient over time by the provider entity 602. In various embodiments, a patient is determined to be compliantly serviced or treated if at least a threshold number of procedural record objects 610 that identify the patient describe treatments that are substantially similar and/or the same as at least one treatment described by the guideline data objects 505 associated with the group to which the patient belongs. That is, a patient may be determined to be compliantly serviced or treated if the patient is associated with at least a threshold number of compliant procedural record data objects 610. In such embodiments, the threshold number of procedural record data objects 610 may be configurable.

Process 700 then includes step/operation 703, which comprises generating a compliance score for the provider entity 602 with respect to the given service need condition. The compliance score is generated based at least in part on weighting the percentage of compliant procedural record data objects for each group or the percentage of compliantly-serviced patients for each group by significance values of the guideline data objects 505. For example, for a group of procedural record data objects 610 grouped according to an applicable patient cohort of a guideline data object 505, the percentage of compliant procedural record data object 610 within the group is weighted according to the significance value of the guideline data objects 505. As a similar non-limiting example, for a group of patients grouped according to an applicable patient cohort of a guideline data object 505, the percentage of compliantly-served patients within the group is weighted according to the significance value of the guideline data objects 505.

In various embodiments, the compliance score with respect to the given service need condition is then generated based at least in part on a combination (e.g., an averaging, a sum) of the weighted percentages for each group. In various embodiments, steps/operations of process 700 may be performed for each of a set of service need conditions, such that multiple compliance scores for the provider entity 602 each corresponding to a different service need condition are generated to form a compliance profile data object 605.

In general, generation of a compliance score for a provider entity 602 with respect to a given service need condition is provided by Equation (1), in which comp represents the compliance score, $c_g$ represents the compliance percentage (e.g., percentage of complaint procedural record data objects 610, percentage of compliantly-served patients) within a group g, and $w_g$ represents the significance value of the guideline data object 505 for the group g. In some examples, multiple guideline data objects 505 may be associated with the group g, and $w_g$ may represent an average of the significance values of the multiple guideline data objects 505.

$$\text{comp} = \Sigma_g c_g * w_g / \Sigma_g w_g \quad \text{Equation (1)}$$

Thus, each provider entity 602 may be associated with a compliance profile data object 605, and the compliance profile data object may be used as an evaluation metric for each provider entity 602. In various embodiments, the client computing entity 102 is operated by a party interested in evaluation of a provider entity 602, and the compliance profile data object 605 is provided (e.g., transmitted) automatically to the client computing entity 102, such as via an API response to an API query.

In various embodiments, the compliance profile data object 605 generated for a provider entity 602 is evaluated for malpractice detection. For instance, if a provider entity 602 has unsatisfactory compliance scores across a significant number of service need conditions, the provider entity 602 may be willfully or ignorantly guilty of malpractice. In various embodiments, the compliance profile data object 605 is provided to a classification machine learning model that may be configured (e.g., using supervised training) to output a binary prediction of whether a provider entity 602 is guilty of malpractice based at least in part on the compliance profile data object 605.

Returning to FIG. 4, process 400 further comprises step/operation 403. Step/operation 403 comprises selecting a subset of the plurality of provider entities 602 based at least in part on the compliance profile data object 605 for each provider entity 602. That is, a subset of provider entities may be recommended for a subject patient based at least in part on their compliance profile data objects 605.

In various embodiments, the subset of provider entities 602 is specifically selected based at least in part on their compliance with respect to specific service need conditions that are determined to be relevant to the subject patient. In doing so, various embodiments involve generation of a patient condition profile data object that describes which service need conditions are relevant to the subject patient. Specifically, a patient condition profile data object may include a deterministic flag for each of a set of service need conditions to indicate whether or not the service need condition is relevant to the subject patient, such as whether or not the subject patient has been diagnosed with the service need condition. For example, the procedural record data object 610 that identifies the subject patient may be retrieved and analyzed to identify past diagnoses of any service need conditions.

Further, the patient condition profile data object may include a predicted risk value for each of the set of service need conditions to indicate a measured probability of the subject patient being diagnosed and/or developing a service need condition in the near future. In various embodiments, the predicted risk value with respect to a particular service need condition is generated based at least in part on a risk scoring and/or a risk prediction machine learning model. Such a risk scoring and/or a risk prediction machine learning model is configured (e.g., trained) to process procedural record data objects 610 associated with the subject patient in order to output a predicted risk value. In some example embodiments, the risk scoring and/or risk prediction machine learning model comprises a LSTM mechanism, an attention mechanism, an RNN mechanism, and/or the like to generate a predicted risk value based at least in part on temporal and/or sequential trends over a plurality of procedural record data objects 610.

Thus, in various embodiments, the subject patient for whom the provider entities 602 are being recommended is associated with a patient condition profile data object that describes an extent to which certain service need conditions are relevant to the subject patient. In various embodiments, the compliance profile data objects 605 of provider entities 602 are weighted according to the patient condition profile data object to enable selection, or at least prioritization, of provider entities 602 that are compliant with respect to service need conditions specifically relevant to the subject patient.

FIG. 8 illustrates an exemplary diagram of selection of provider entities 602 based at least in part on provider compliance. To be specific, FIG. 8 illustrates a recommendation architecture 800 for selection of provider entities 602 for recommendation based at least in part on factors including provider compliance, reviews of provider entities 602, matching between patient and provider entity 602, and/or the like. As illustrated, the recommendation architecture 800 includes the compliance evaluation system 101, which is configured to generate compliance profile data object 605 for each provider entity 602 based at least in part on procedural record data objects 610 (e.g., claims data, EMR data) that describe treatments provided by each provider entity 602, in an example embodiment. In various embodiments, the entirety of the recommendation architecture 800 may be embodied within the compliance evaluation system 101 and/or the system computing entity 106.

At block 805, the compliance profile data objects 605 for the provider entities 602 are evaluated with various other factors in order to provide a recommendation list 810 of recommended provider entities 602 for the subject patient. In various embodiments, the recommendation architecture 800 includes a multi-attribute content search and filtering system which enables user so the recommendation architecture 800 (e.g., the subject patient themselves, an administrator, emergency services) to explicitly provide general preferences on multi-attribute characteristics of provider entities 602 that can be used by various searching and filtering techniques to supplement selection of provider entities 602 for recommendation. This defined filter may be applied to the set of the provider entities 602 prior to generation of compliance profile data objects 605 and generation of other representations and vectorizations of the provider entities 602, in some example embodiments. Example attribute characteristics that can be filtered as defined by a user may include provider gender, age range, specialization, facility type, maximum distance, provider network type (e.g., based at least in part on a healthcare insurance plan or network of the subject patient), and/or the like.

In various embodiments, a patient-provider match score M may be defined as a weighted sum of matching criteria, such as the semantic similarity of the subject patient's condition to the provider's specialty or the proximity of the subject patient's home to the provider's location. In various embodiments, the patient-provider match score M may also be determined using the patient condition profile data object 815 describe the relevant service need conditions to the subject patient. In doing so, M incorporates the subject patient's risk factor for a given diagnosis in order to account for potential severity of the member's diagnosis. In an example embodiment, Equation (2) may be used to determine the patient-provider match score M as a weighted sum of matching criteria $F_i$.

$$M=\Sigma_i w_i * F_i \quad \text{Equation (2)}$$

As illustrated in FIG. 8, an overall score R may be assigned to each provider entity 602 by factoring in patient-provider match score M in combination with the compliance profile data object 605. The overall score R is further based at least in part on the qualifications Q of the provider entity 602, such as education, publication record, number of researching projects, awards, ratings, and/or the like, as well as patient satisfaction with the provider entity 602 as evidence through received feedback and patient surveys. In an example embodiment, Equation (3) may be used to determine the overall score R of a provider entity 602.

$$R=\omega_m*M+\omega_Q*Q+\omega_{reviews}*\text{Reviews}+\omega_{comp}*\text{comp} \quad \text{Equation (3)}$$

In Equation (3), $\omega_M$, $\omega_Q$, $\omega_{reviews}$, $\omega_{comp}$ are configurable weights enabling configuration of recommendation criteria importance.

In various embodiments, the overall score R for each provider entity 602 is used to select a subset of the plurality of provider entities 602. Provider entities 602 may be ranked with respect to R, and a configurable number of top-ranked provider entities 602 are selected for the subset. In another example embodiment, a score threshold is configured, and any provider entity 602 having a score R satisfying the score threshold is selected for the subset.

FIG. 8 additionally illustrates malpractice-based actions 820 within the recommendation architecture 800. As previously described, the compliance evaluation system 101 may output a compliance profile data object 605 for a provider entity 602, which includes compliance scores for each of a plurality of different service need conditions. In the illustrated embodiment, a malpractice-based action 820 may be performed if the compliance profile data object 605 does not satisfy one or more malpractice thresholds. For example, if one compliance score for a particular service need condition is negative or otherwise indicates low compliance to guidelines, malpractice-based actions 820 may be performed. As another non-limiting example, the compliance profile data object 605 including at least a threshold number of compliance scores that indicate low compliance may cause malpractice-based actions 820 to be performed. As yet another example, an average of the compliance scores not satisfying a malpractice threshold may cause a malpractice-based action 820 to be performed. Example malpractice-based actions may include generating and providing a malpractice report to a governing entity, automatically notifying the provider entity, automatically providing clinical guidelines resources to the provider entity, removal of the provider entity from service networks, and/or the like.

Accordingly, various embodiments of the present invention address technical challenges related to improving computational efficiency, operational reliability, and operational throughput of predictive recommendation systems. By disclosing techniques for generating more effective recommendations, various embodiments of the present invention reduce the number of repeated queries by end-users to generate predictive recommendations. This in turn: (i) decreases the number of computational operations performed by processing units of predictive recommendation systems, thus increasing the computational efficiency of predictive recommendation systems, (ii) decreases the overall likelihood of system failure given a constant per-recommendation likelihood failure, thus increasing operational reliability of predictive recommendation systems, and (iii) increases the overall number of end-users that the predictive recommendation system can serve given a constant per-user query count, thus increasing the operational throughput of predictive recommendation systems. Accordingly, various embodiments of the present invention make important technical contributions to the field of predictive data analysis by improving computational efficiency, operational reliability, and operational throughput of predictive recommendation systems.

Returning to FIG. 4, process 400 further includes step/operation 404, which includes performing at least one recommendation-based action with the selected subset. In various embodiments, the subset of provider entities 602 (e.g., a list of unique identifiers such as NPI numbers) is provided to a client computing entity 102 via an API response. In various embodiments, a notification may be automatically generated at a client computing entity 102 associated with the subject patient to alert the subject patient to the recommended providers. In some example instances, emergency services request provider recommendation for a subject patient, and in various embodiments, directions and routing to a recommended provider entity 602 are automatically provided to the emergency services (e.g., an ambulance) to assist transport of the subject patient to the provider entity 602. In further example instances, each recommended provider entity 602 may be notified (e.g., via an associated computing entity) that the provider entity 602 was recommended to a subject patient, and with such notification, subject patient information, such as demographic information, biometric information, diagnoses, and/or the like may be provided to the provider entity 602.

Examples of prediction-based actions performed based at least in part on the selected subset comprise retrieving data associated with the provider entities in the selected subset and saving the noted data on a local storage medium of a query-initiating client device for more efficient retrieval. Other examples of prediction-based actions based at least in part on one or more output data items of various embodiments of the present invention include automatic appointment scheduling, automatic operational load balancing institutions for server systems associated with provider institutions such as hospitals, automatic drug prescription delivery, and/or the like.

Therefore, various embodiments of the present disclosure provide various technical advantages and technical solutions through recommending healthcare providers at least according to provider compliance with established clinical guidelines for medical treatment. Recommendation quality and accuracy through provider compliance and incorporation thereof with other features reduces overall system load and user interaction through improvement to user satisfaction. For instance, improved recommendation of healthcare providers reduces an amount of user inquiries regarding alternative providers received by a provider recommendation system, as well as reduces a total amount of data processing, transmission, and communication prompted from users requesting transitions between different providers frequently.

As further described above, various embodiments of the present disclosure address technical challenges related to improving computational efficiency, operational reliability, and operational throughput of predictive recommendation systems. By disclosing techniques for generating more effective recommendations, various embodiments of the present invention reduce the number of repeated queries by end-users to generate predictive recommendations. This in turn: (i) decreases the number of computational operations performed by processing units of predictive recommendation systems, thus increasing the computational efficiency of predictive recommendation systems, (ii) decreases the overall likelihood of system failure given a constant per-recommendation likelihood failure, thus increasing operational reliability of predictive recommendation systems, and (iii) increases the overall number of end-users that the predictive recommendation system can serve given a constant per-user query count, thus increasing the operational throughput of predictive recommendation systems. Accordingly, various embodiments of the present invention make important technical contributions to the field of predictive data analysis by improving computational efficiency, operational reliability, and operational throughput of predictive recommendation systems.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method comprising:
   generating, by one or more processors and using a natural language processing (NLP) model, a guideline vector for a service need condition from reference data associated with the service need condition, wherein the service need condition is one of a plurality of service need conditions;
   generating, by the one or more processors, a compliance profile vector for a provider entity, wherein the compliance profile vector comprises a plurality of compliance scores for the provider entity with respect to the plurality of service need conditions, and wherein generating the compliance profile vector comprises:
      for the service need condition: (i) retrieving one or more procedural record data objects each describing a treatment provided by the provider entity for the service need condition, and (ii) determining a compliance score from the plurality of compliance scores for the service need condition using the one or more procedural record data objects and the guideline vector, and
      determining the compliance profile vector based at least in part on the compliance score;
   selecting, by the one or more processors, the provider entity from a plurality of provider entities based on a vector comparison between the compliance profile vector and a plurality of compliance profile vectors respectively corresponding to the plurality of provider entities; and
   performing an automated recommendation-based action based at least in part on the selected provider entity.

2. The computer-implemented method of claim 1, wherein the guideline vector describes a plurality of applicable patient cohorts and a plurality of significance values.

3. The computer-implemented method of claim 2, wherein determining the compliance score of the selected provider entity for the service need condition comprises:
   grouping the one or more procedural record data objects according to the plurality of applicable patient cohorts described by the guideline vector for the service need condition;
   determining a percentage of compliant procedural record data objects within each group based at least in part on a comparison of the treatment described by a procedural record data object for the service need condition with the guideline vector for the service need condition; and generating the compliance score for the service need condition based at least in part on weighting the percentage for each group according to the plurality of significance values described by the guideline vector.

4. The computer-implemented method of claim 1, further comprising:
automatically identifying malpractice of the selected provider entity according to one or more negatively-valued compliance scores of the compliance profile vector; and
performing at least one automated malpractice-based action with respect to the selected provider entity.

5. The computer-implemented method of claim 1, further comprising generating a patient condition profile data object comprising one or more risk values for the plurality of service need conditions.

6. The computer-implemented method of claim 5, wherein the selected provider entity is selected based at least in part on the plurality of compliance scores of the compliance profile vector with respect to the one or more risk values of the patient condition profile data object.

7. The computer-implemented method of claim 6, wherein the selected provider entity is selected further based at least in part on demographic information associated with the selected provider entity.

8. The computer-implemented method of claim 1, wherein the guideline vector is generated based at least in part on (i) providing at least a portion of the reference data for display to a user, and (ii) receiving user input from the user defining the guideline vector.

9. The computer-implemented method of claim 1, wherein the automated recommendation-based action comprises automatically transmitting a provider identifier configured to identify the selected provider entity or the compliance profile vector associated with the selected provider entity via an application programing interface (API) response to a received API query.

10. A computing system comprising one or more processors and memory, the one or more processors configured to, with the memory cause the computing system to:
generate, using a natural language processing (NLP) model, a guideline vector for a service need condition from reference data associated with the service need condition, wherein the service need condition is one of a plurality of service need conditions;
generate a compliance profile vector for a provider entity, wherein the compliance profile vector comprises a plurality of compliance scores for the provider entity with respect to the plurality of service need conditions, and wherein, to generate the compliance profile vector, the one or more processors are further configured to cause the computing system to:
for the service need condition: (i) retrieve one or more procedural record data objects each describing a treatment provided by the provider entity for the service need condition, and (ii) determine a compliance score from the plurality of compliance scores for the service need condition using the one or more procedural record data objects and the guideline vector, and
determine the compliance profile vector based at least in part on the compliance score;
select the provider entity from a plurality of provider entities based on a vector comparison between the compliance profile vector and a plurality of compliance profile vectors respectively corresponding to the plurality of provider entities; and perform an automated recommendation-based action based at least in part on the selected provider entity.

11. The computing system of claim 10, wherein the guideline vector describes a plurality of applicable patient cohorts and a plurality of significance values.

12. The computing system of claim 11, wherein, to determine the compliance score of the selected provider entity for the service need condition, the one or more processors are further configured to cause the computing system to:
group the one or more procedural record data objects according to the plurality of applicable patient cohorts described by the guideline vector for the service need condition;
determine a percentage of compliant procedural record data objects within each group based at least in part on a comparison of the treatment described by a procedural record data object for the service need condition with the guideline vector for the service need condition; and
generate the compliance score for the service need condition based at least in part on weighting the percentage for each group according to the plurality of significance values described by the guideline vector.

13. The computing system of claim 10, wherein the one or more processors are further configured to cause the computing system to:
automatically identify malpractice of the selected provider entity according to one or more negatively-valued compliance scores of the compliance profile vector; and
perform at least one automated malpractice-based action with respect to the selected provider entity.

14. The computing system of claim 10, wherein the one or more processors are further configured to cause the computing system to generate a patient condition profile data object comprising one or more risk values for the plurality of service need conditions.

15. The computing system of claim 14, wherein the selected provider entity is selected based at least in part on the plurality of compliance scores of the compliance profile vector with respect to the one or more risk values of the patient condition profile data object.

16. The computing system of claim 15, wherein the selected provider entity is selected further based at least in part on demographic information associated with the selected provider entity.

17. The computing system of claim 10, wherein the guideline vector is generated based at least in part on (i) providing at least a portion of the reference data for display to a user, and (ii) receiving user input from the user defining the guideline vector.

18. The computing system of claim 10, wherein the automated recommendation-based action comprises automatically transmitting a provider identifier configured to identify the selected provider entity or the compliance profile vector associated with the selected provider entity via an application programing interface (API) response to a received API query.

19. A non-transitory computer-readable storage medium including instructions that when executed by one or more processors, cause the one or more processors to:
generate, using a natural language processing (NLP) model, a guideline vector for a service need condition from reference data associated with the service need condition, wherein the service need condition is one of a plurality of service need conditions;

generate a compliance profile vector for a provider entity, wherein the compliance profile vector comprises a plurality of compliance scores for the provider entity with respect to the plurality of service need conditions, and wherein, to generate the compliance profile vector, the one or more processors are further configured to cause the computing system to:
  for the service need condition: (i) retrieve one or more procedural record data objects each describing a treatment provided by the provider entity for the service need condition, and (ii) determine a compliance score from the plurality of compliance scores for the service need condition using the one or more procedural record data objects and the guideline vector, and
  determine the compliance profile vector based at least in part on the compliance score;
select the provider entity from a plurality of provider entities based on a vector comparison between the compliance profile vector and a plurality of compliance profile vectors respectively corresponding to the plurality of provider entities; and
perform an automated recommendation-based action based at least in part on the selected provider entity.

* * * * *

UNITED STATES PATENT AND TRADEMARK OFFICE
CERTIFICATE OF CORRECTION

| | |
|---|---|
| PATENT NO. | : 12,136,489 B2 |
| APPLICATION NO. | : 17/528041 |
| DATED | : November 5, 2024 |
| INVENTOR(S) | : Karim Mahmoud Mohamed Moustafa et al. |

It is certified that error appears in the above-identified patent and that said Letters Patent is hereby corrected as shown below:

In the Claims

In Column 29, Line 36, Claim 9, delete "programing" and insert -- programming --, therefor.

In Column 29, Line 40, Claim 10, delete "memory cause" and insert -- memory, cause --, therefor.

In Column 30, Line 58, Claim 18, delete "programing" and insert -- programming --, therefor.

Signed and Sealed this
Twenty-first Day of January, 2025

Coke Morgan Stewart
*Acting Director of the United States Patent and Trademark Office*